(12) United States Patent  
Shimono

(10) Patent No.: US 7,729,468 B2  
(45) Date of Patent: Jun. 1, 2010

(54) X-RAY TOMOGRAPH AND STEREORADIOSCOPIC IMAGE CONSTRUCTION EQUIPMENT

(75) Inventor: Takashi Shimono, Nasushiobara (JP)

(73) Assignees: Kabushiki Kaisha Toshiba, Tokyo (JP); Toshiba Electron Tubes & Devices Co., Ltd., Tochiqi (JP)

( * ) Notice: Subject to any disclaimer, the term of this patent is extended or adjusted under 35 U.S.C. 154(b) by 329 days.

(21) Appl. No.: 10/590,517

(22) PCT Filed: Feb. 25, 2005

(86) PCT No.: PCT/JP2005/003199

§ 371 (c)(1),  
(2), (4) Date: Aug. 24, 2006

(87) PCT Pub. No.: WO2005/083403

PCT Pub. Date: Sep. 9, 2005

(65) Prior Publication Data

US 2008/0267347 A1 Oct. 30, 2008

(30) Foreign Application Priority Data

Feb. 27, 2004 (JP) .............................. 2004-054625

(51) Int. Cl.  
*A61B 6/00* (2006.01)  
*G01N 23/00* (2006.01)  
*G21K 1/12* (2006.01)  
*H05G 1/60* (2006.01)

(52) U.S. Cl. .............................. 378/10; 378/21; 378/137

(58) Field of Classification Search .................. 378/10, 378/21, 22, 25, 137  
See application file for complete search history.

(56) References Cited

U.S. PATENT DOCUMENTS

| 3,973,127 A | * | 8/1976 | Matsuda et al. ................ 378/24 |
| 4,105,922 A | * | 8/1978 | Lambert et al. ............. 382/131 |
| 4,926,452 A | | 5/1990 | Baker et al. |
| 5,081,656 A | | 1/1992 | Baker et al. |
| 5,097,492 A | | 3/1992 | Baker et al. |
| 5,259,012 A | | 11/1993 | Baker et al. |
| 5,278,884 A | * | 1/1994 | Eberhard et al. ................ 378/4 |
| 5,291,535 A | | 3/1994 | Baker et al. |

(Continued)

FOREIGN PATENT DOCUMENTS

DE 28 15218 C2 10/1978

(Continued)

*Primary Examiner*—Hoon Song  
*Assistant Examiner*—Mona M Sanei  
(74) *Attorney, Agent, or Firm*—Pillsbury Winthrop Shaw Pittman, LLP

(57) ABSTRACT

An X-ray tomograph comprises an X-ray generator having a function of moving the focal position and radiating X-rays toward a subject, an X-ray image receiving element for receiving transmission images created by X-rays radiated from the X-ray generator, and an image processing section for creating a tomographic image by processing the transmission images of the subject received by the X-ray image receiving element. A stereoradioscopic image constructing equipment comprises the X-ray tomograph and a stereoradioscopic image constructing section for creating a stereoradioscopic image by subjecting the created tomographic images to image processing. By using the X-ray tomograph, a tomographic image can be created without providing any high-precision movable mechanism, and a tomographic image of even a soft subject can be correctly created.

6 Claims, 11 Drawing Sheets

U.S. PATENT DOCUMENTS

| | | | |
|---|---|---|---|
| 5,561,696 A | | 10/1996 | Adams et al. |
| 5,594,768 A | * | 1/1997 | Fujii et al. .................... 378/21 |
| 5,621,811 A | | 4/1997 | Roder et al. |
| 6,002,739 A | | 12/1999 | Heumann |
| 6,483,890 B1 | * | 11/2002 | Malamud .................... 378/22 |
| 2008/0247505 A1 | * | 10/2008 | Patnaik et al. ................. 378/10 |

FOREIGN PATENT DOCUMENTS

| | | | |
|---|---|---|---|
| DE | 38 54 865 T2 | | 6/1996 |
| EP | 0 053 943 B1 | | 7/1986 |
| GB | 1 599 484 | | 10/1981 |
| JP | 53140988 | | 12/1978 |
| JP | 2501411 | | 5/1990 |
| JP | 5503652 | | 6/1993 |
| JP | 7005125 | | 1/1995 |
| JP | 11339050 | | 12/1999 |
| JP | 2003-024320 | * | 1/2003 |
| WO | WO 89/04477 | | 5/1989 |
| WO | WO 92/03969 | | 3/1992 |

* cited by examiner

X-RAY TOMOGRAPH AND STEREORADIOSCOPIC IMAGE CONSTRUCTION EQUIPMENT

This is the U.S. National Stage of International Patent Application No. PCT/JP2005/003199, filed on Feb. 25, 2005, which relies for priority upon Japanese Patent Application No. 2004-054625, filed on Feb. 27, 2004, the contents of both of which are incorporated herein by reference in their entireties.

TECHNICAL FIELD

The present invention relates to an X-ray tomograph for creating a tomographic image by processing plural transmission images received by radiating X-rays and to a stereoradioscopic image constructing equipment provided with the X-ray tomograph.

BACKGROUND ART

Conventionally, an X-ray tomograph is used to inspect, for example, the inside structure of a subject without destruction. The X-ray tomograph comprises an X-ray generator for radiating X-rays to a subject and an X-ray image receiving element for receiving transmission images formed by the X-rays radiated from the X-ray generator. The X-ray generator is configured to be rotatable around the subject on the same plane by a mechanical movable mechanism. The X-ray image receiving element can be rotated by a mechanical movable mechanism in correspondence with the movement of the X-ray generator. Besides, the X-ray image receiving element is connected to an image processing device which processes the transmission images received by the X-ray image receiving element to create a tomographic image. (See, for example, Patent Document 1)

But, a method using the above X-ray tomograph has a disadvantage that a high-precision movable mechanism must be used to rotate the X-ray generator and the X-ray image receiving element in order to keep a spatial resolution of several micrometers.

The subject may be rotated and translated instead of the rotations of the X-ray generator and the X-ray image receiving element, but such a method needs a high-precision movable mechanism for rotation of the subject and has a disadvantage that it cannot be used for examination of, for example, a soft subject which is deformed when rotated.

Patent Document 1: JP-A 2-501411 (page 12 and FIG. 1)

DISCLOSURE OF THE INVENTION

The present invention has been made to solve these problems, and an object thereof is to provide an X-ray tomograph that can provide a tomographic image without having a high-precision movable mechanism and also obtain a tomographic image of a soft subject, and a stereoradioscopic image constructing equipment having the X-ray tomograph.

The X-ray tomograph of the invention comprises an X-ray generator having a function of moving a focal position and radiating X-rays toward a subject, an X-ray image receiving element for receiving a plurality of transmission images of the subject formed by the X-rays radiated from the X-ray generator while the focal position is moved, and an image processing section for creating a tomographic image by processing the plurality of transmission images of the subject received by the X-ray image receiving element.

The stereoradioscopic image constructing equipment of the invention comprises the above-described X-ray tomograph of the invention, and a stereoradioscopic image constructing section for creating a stereoradioscopic image by processing the plurality of tomographic images created by the X-ray tomograph.

According to the present invention, the tomographic image of the subject can be obtained easily without provision of a movable mechanism for moving, for example, an X-ray generator, an X-ray image receiving element or a subject by radiating the X-rays to the subject while moving a focal position of the X-ray generator, receiving by the X-ray image receiving element the plural transmission images of the subject formed by the X-rays from the different focal positions, and processing the received transmission images by the image processing section to create the tomographic image. A tomographic image of, for example, a soft subject can also be obtained securely.

BEST MODE FOR CARRYING OUT THE INVENTION

Preferred embodiments of the invention will be described with reference to the drawings. It is to be understood that the present invention is not limited to the following embodiments.

Figure 1:
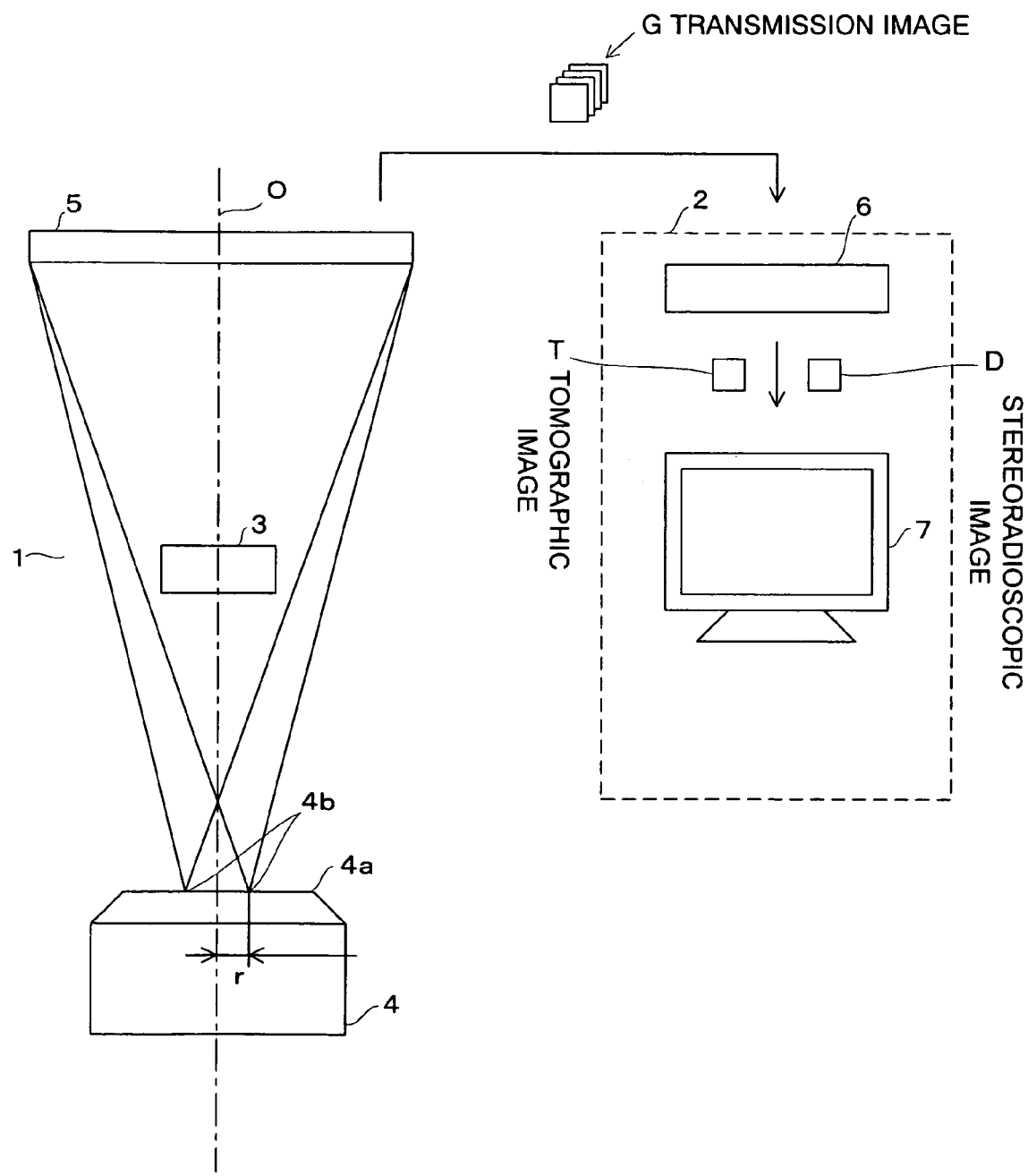
FIG. 1 is an explanatory view showing a stereoradioscopic image constructing equipment according to one embodiment of the invention.

FIG. 1 shows the stereoradioscopic image constructing equipment of one embodiment of the invention. This stereoradioscopic image constructing equipment is provided with an X-ray CT (computed tomography) apparatus 1 as an X-ray tomograph and an image processing device 2. The stereoradioscopic image constructing equipment is used for nondestructive inspection or the like of a subject 3.

The X-ray CT apparatus 1 is provided with an X-ray tube 4 as an X-ray generator and an X-ray image receiving element 5. The X-ray tube 4 and the X-ray image receiving element 5 are disposed to face each other, and the X-ray image receiving element 5 is connected to the image processing device 2. The subject 3 is disposed between the X-ray tube 4 and the X-ray image receiving element 5 and fixed on a fixing stand such as an X-Y-Z table (not shown).

The X-ray tube 4 is formed to have a substantially cylindrical shape and disposed such that a central axis O agrees substantially with the center of the X-ray image receiving element 5. The X-ray tube 4 has a radiation plane 4a which is parallel to the X-ray image receiving element 5. The radiation plane 4a has an X-ray generating source 4b as a focal point for generation of X-rays toward the subject 3. The X-ray generating source 4b is disposed to be rotatable on a circumference having a prescribed radius r with the central axis O of the X-ray tube 4 as the center on the radiation plane 4a. In other words, the X-ray tube 4 has a function to move the positions of the X-ray generating source 4b, and the X-ray generating source 4b is configured to be rotatable, for example, one degree at a time with respect to the central axis O along the entire circumference, namely 360 degrees.

The X-ray image receiving element 5 is, for example, a square planar image intensifier or a planar X-ray detector, and receives an X-ray image, which has passed through the subject 3 after radiation from the X-ray generating source 4b of the X-ray tube 4, upon converting into a transmission image G which is an image signal. And, the transmission image G is sent to the image processing device 2.

The image processing device 2 has a computer 6 as a processing arithmetic logic unit and a monitor 7 as an image display part connected to the computer 6. The computer 6 processes the transmission image G transmitted from the X-ray image receiving element 5 and has an image processing section and a stereoradioscopic image constructing section.

Figure 2:
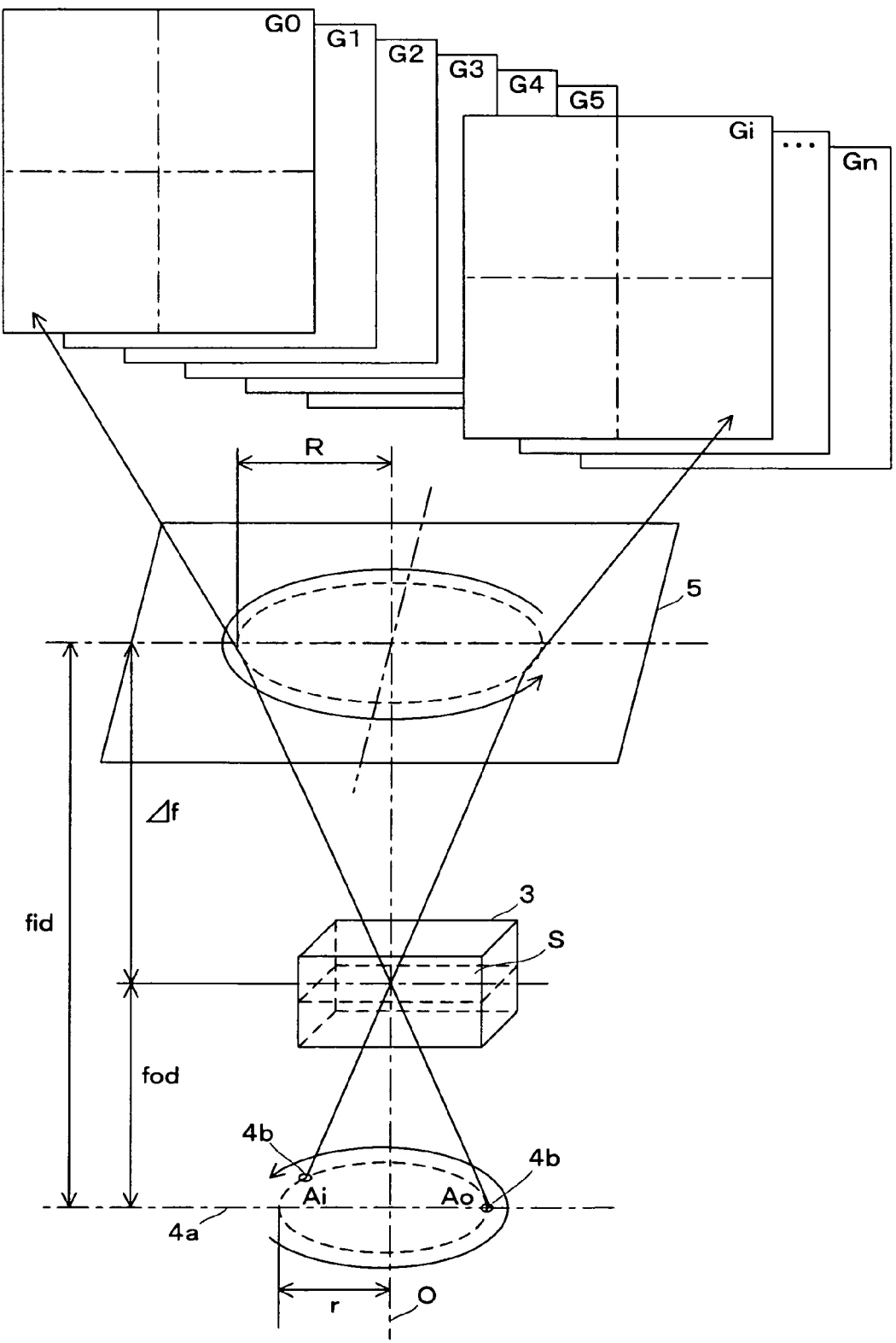
FIG. 2 is an explanatory diagram showing an X-ray tomograph of the stereoradioscopic image constructing equipment according to the embodiment of the invention.
Figure 3:
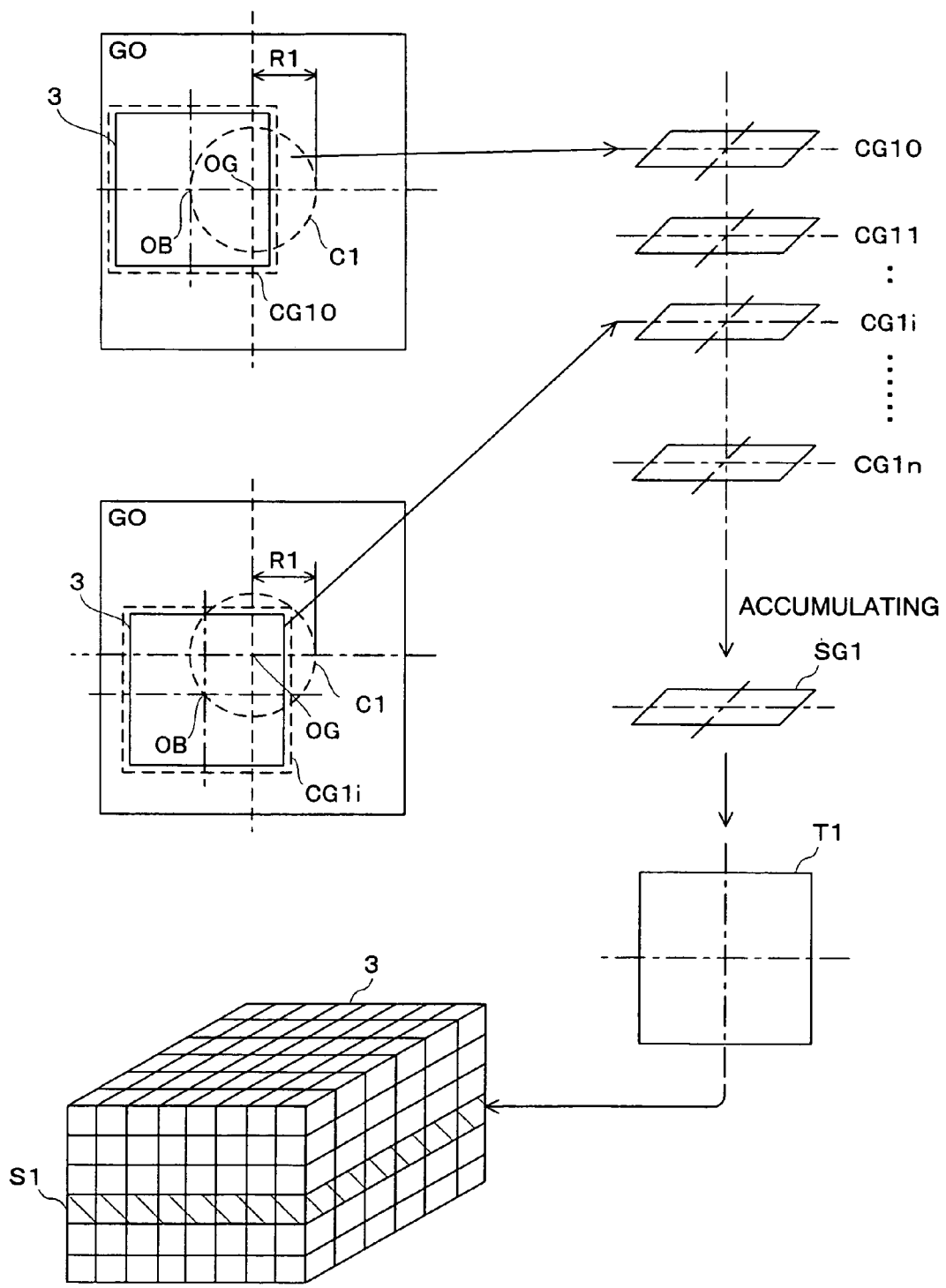
FIG. 3 is an explanatory diagram showing accumulation of transmission images by the X-ray tomograph of the invention.
Figure 4:
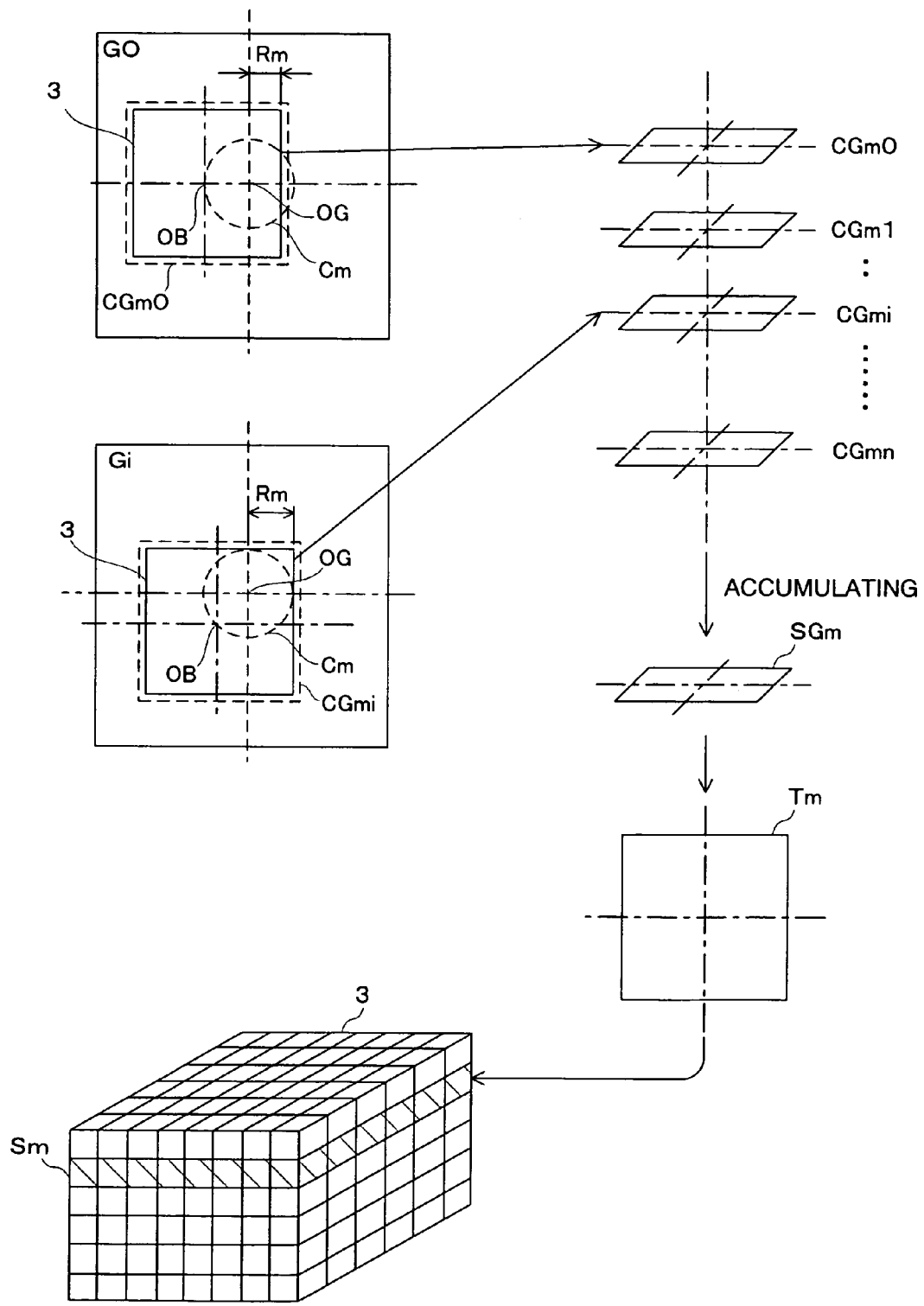
FIG. 4 is an explanatory diagram showing accumulation of other transmission images by the X-ray tomograph of the invention.

The image processing section of the computer 6 cuts out square images from individual transmission images G0, G1, . . . , Gi, . . . , Gn corresponding to individual positions A0, A1, . . . , Ai, . . . , An of the X-ray generating source 4b of the X-ray tube 4 as shown in FIG. 2 through FIG. 4 and accumulates the cut-out images CG to create an accumulated image SG. The images are cut out into a square shape with a virtual center 0B, which is positioned on a circumference having a radius R from a center 0G of the transmission image, determined as the center. The cutout images CG correspond to arbitrary tomographic planes S which intersect in the axial direction of the X-ray tube 4 and are different from one another.

Laminographs, namely tomographic images T, of the subject 3 corresponding to the individual tomographic planes S are created by calculating a brightness value B of each pixel of the obtained accumulated image SG and extracting pixels having the brightness value B which is between a prescribed upper limit threshold value TH and a prescribed lower limit threshold value TL smaller than the upper limit threshold value TH.

Here, a ratio between the radius r and the radius R is indicated as a ratio between a distance fod and a distance $\Delta f$ as shown in FIG. 2. Specifically, it is expressed as $R = r \times \Delta f / fod$, where the distance fod indicates a distance from the radiation plane 4a of the X-ray tube 4 to the tomographic plane S of the subject 3, and the distance $\Delta f$ indicates a difference between the distance fod and a distance fid from the radiation plane 4a of the X-ray tube 4 to the X-ray image receiving element 5. The upper limit threshold value TH and the lower limit threshold value TL are previously determined according to the brightness value B of the pixels of the accumulated image SG.

The stereoradioscopic image constructing section of the computer 6 creates a three-dimensional image, namely a stereoradioscopic image D, by composing upon correcting a geometrical enlargement ratio P of the tomographic images T created by the image processing section for each of the plural tomographic planes S which intersect in the axial direction of the X-ray tube 4 and are different from one another. Here, the geometrical enlargement ratio P is indicated as a ratio between the distance fid (a distance from the radiation plane 4a of the X-ray tube 4 to the X-ray image receiving element 5) and the distance fod (a distance from the radiation plane 4a of the X-ray tube 4 to the tomographic plane S of the subject 3) shown in FIG. 2. Specifically, it is expressed as $P = fid/fod$.

The monitor 7 displays the tomographic images T of the subject 3 and the stereoradioscopic image D created by the computer 6.

An X-ray tomographic process and a stereoradioscopic image constructing process according to an embodiment of the invention will be described with reference to FIG. 2 through FIG. 4.

First, the subject 3 is fixed to the fixing stand, and the rotating radius r of the X-ray generating source 4b of the X-ray tube 4 is determined such that an X-ray is radiated to a prescribed tomographic plane S1 of the subject 3.

Then, an X-ray is radiated from the X-ray generating source 4b located at A0 to the subject 3 as shown in FIG. 2. And, the X-ray generating source 4b is moved, for example, one degree at a time with respect to the central axis O along the circumference with the radius r on the radiation plane 4a, to convert the X-ray image of the subject 3 corresponding to a position Ai into a transmission image Gi.

At this time, the X-ray image receiving element 5 has the center 0B of the X-ray image of the subject 3 positioned on a virtual circumference C1 with a radius R1 corresponding to the position of the tomographic plane S1 with a center 0G of the transmission images G as the center, and the X-ray image of the subject 3 rotates along the circumference about the center 0G of the transmission image G with the movement of the X-ray generating source 4b of the X-ray tube 4.

Then, the computer 6 of the image processing device 2 having received the transmission images G0, G1, . . . , Gi, . . . , Gn cuts out square images with the center 0B, which is positioned on the virtual circle C1 of the radius R1 from the center of the transmission images G0, G1, . . . , Gi, . . . , Gn as a center, and accumulates cutout images CG10, CG11, . . . , CG1i, . . . , CG1n to create an accumulated image SG1.

Figure 5:
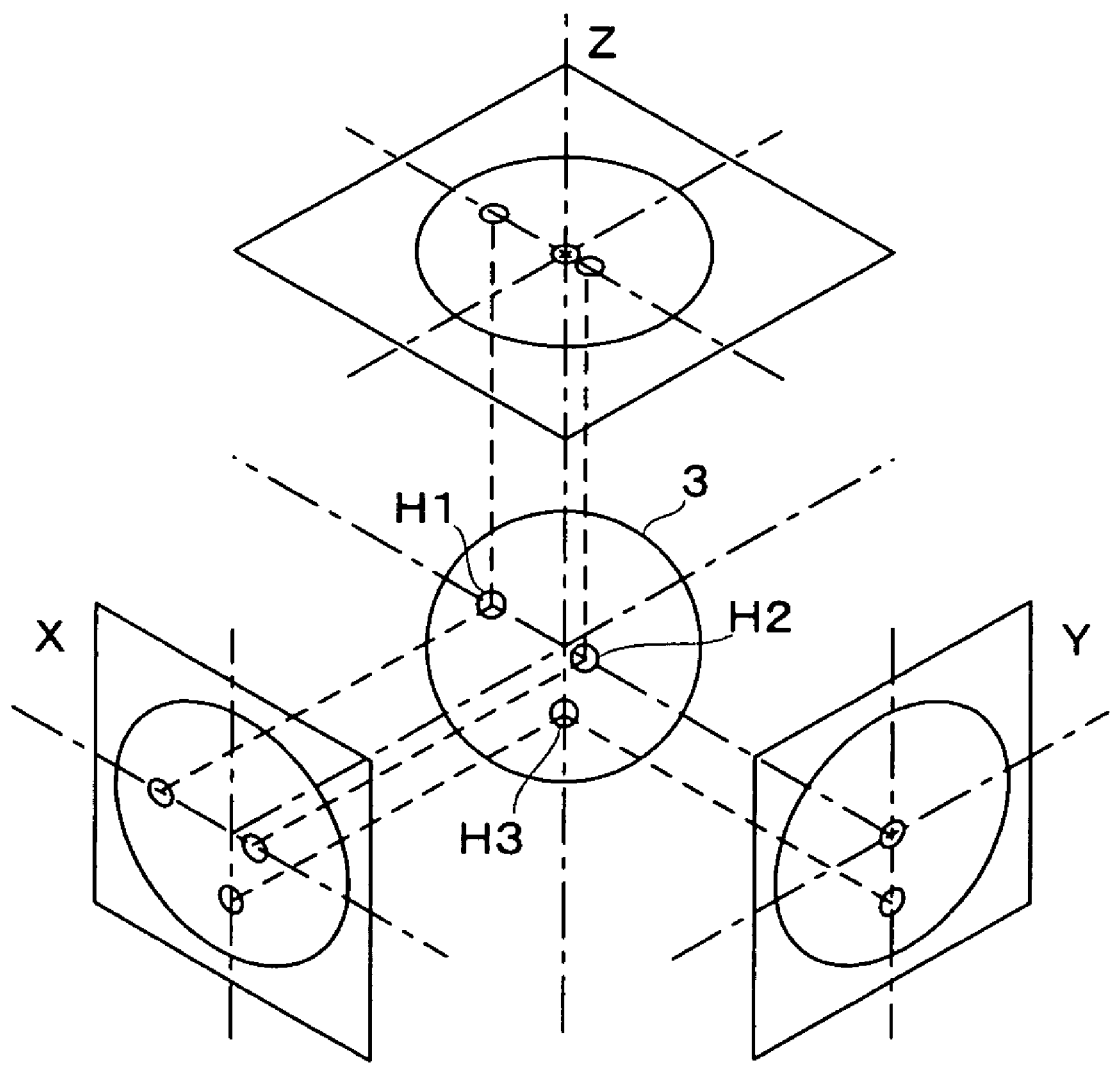
FIG. 5 is a perspective view showing an example of a subject to be examined by the X-ray tomograph of the invention.

Creation of the accumulated image will be described more specifically assuming that the subject 3 has a shape as shown in, for example, FIG. 5 or a shape that a spherical substance has three holes H1, H2, H3 therein.

Figure 6:
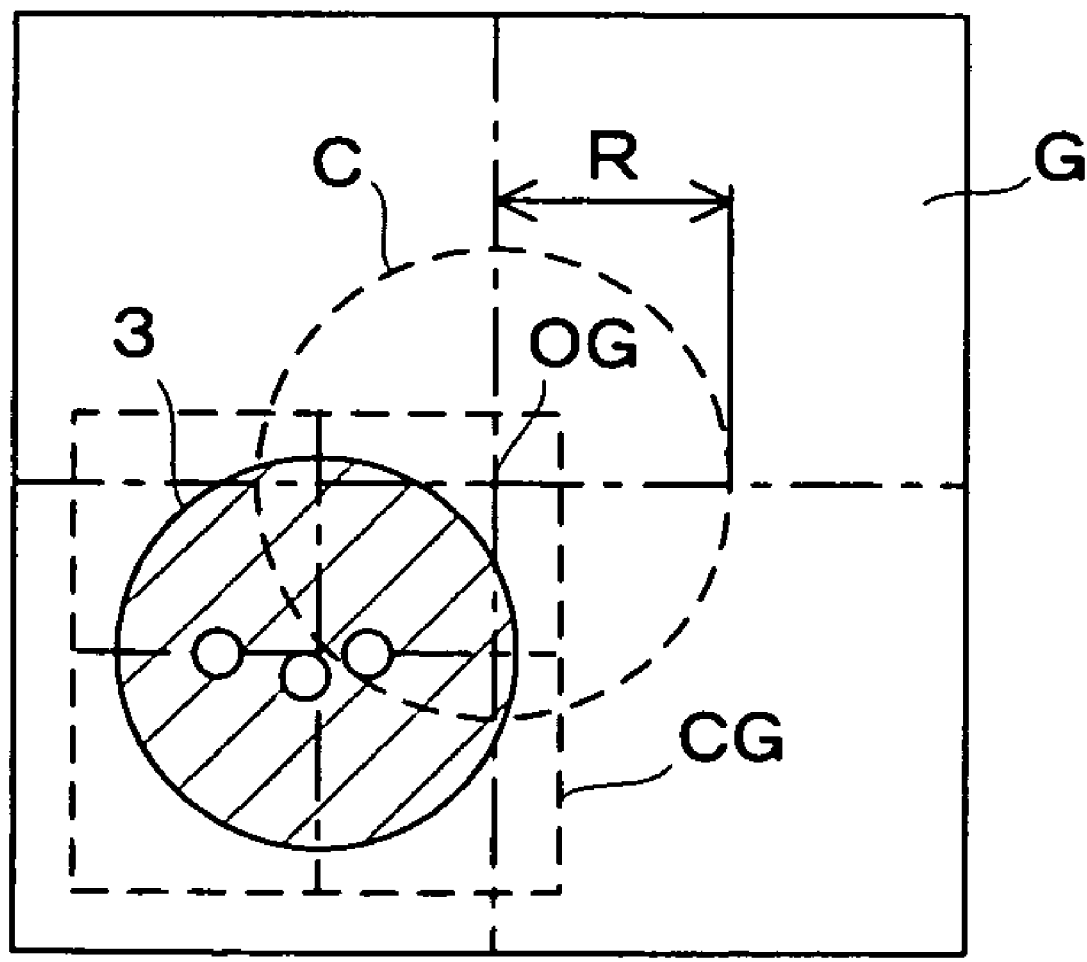
FIG. 6 is a plan view showing a transmission image to be processes by the X-ray tomograph of the invention.
Figure 7:
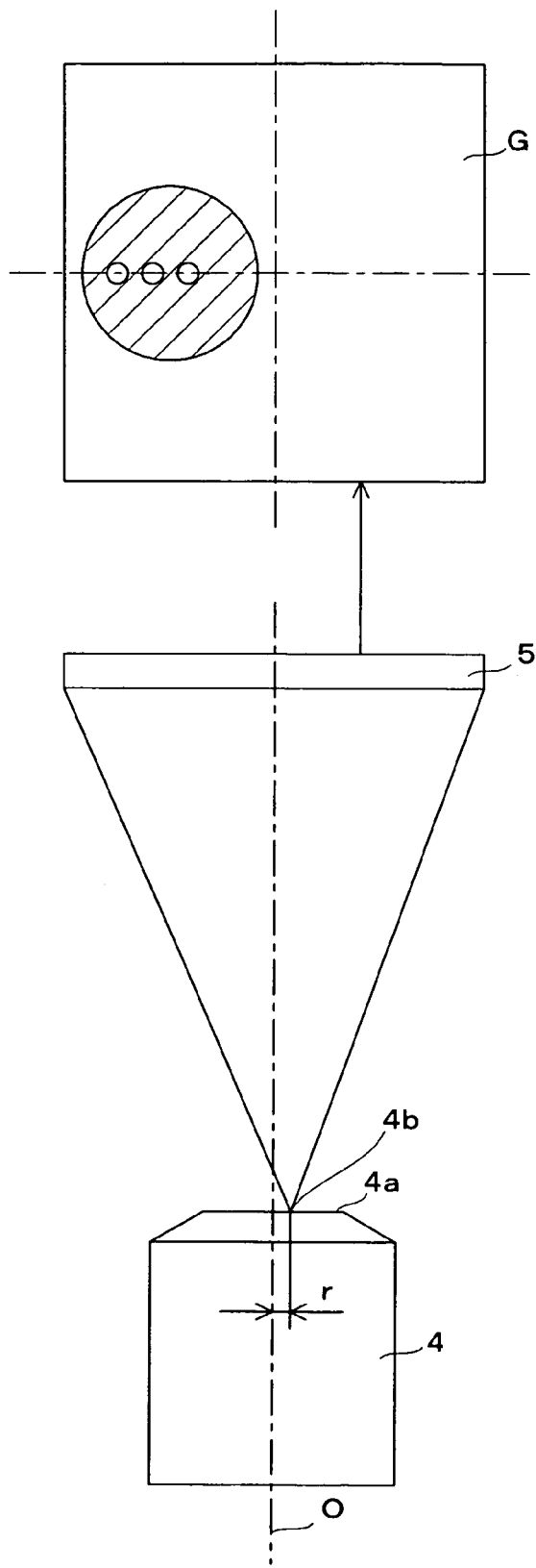
FIG. 7 is an explanatory view showing the X-ray tomograph of the invention and a transmission image of a subject by the X-ray tomograph.
Figure 8A:
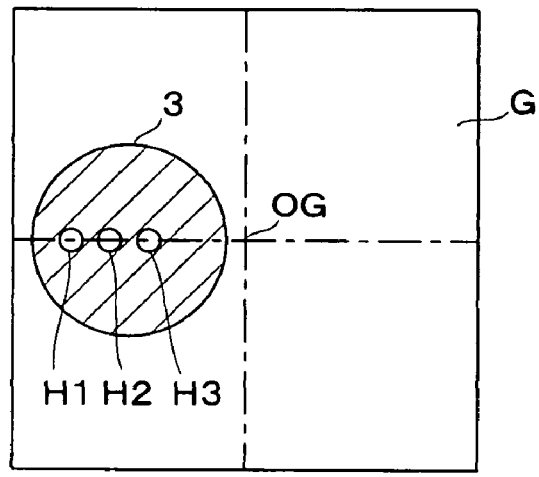
FIG. 8A is a plan view showing a transmission image of a subject when a focal point is at a start position.
Figure 8B:
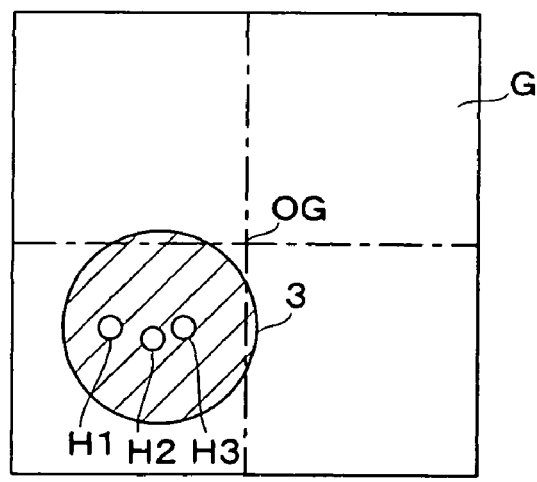
FIG. 8B is a plan view showing a transmission image of the subject when the focal point is rotated 45 degrees with respect to the start position.
Figure 8C:
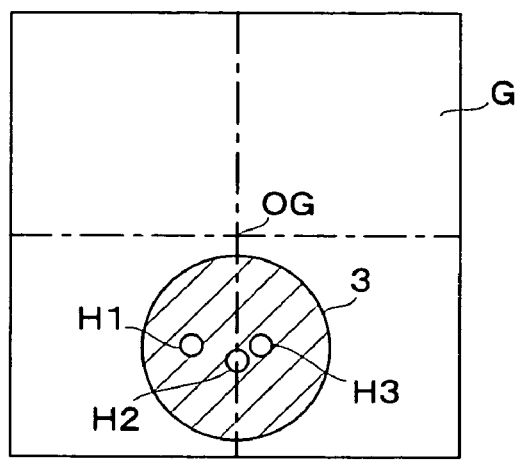
FIG. 8C is a plan view showing a transmission image of the subject when the focal point is rotated 90 degrees with respect to the start position.
Figure 8D:
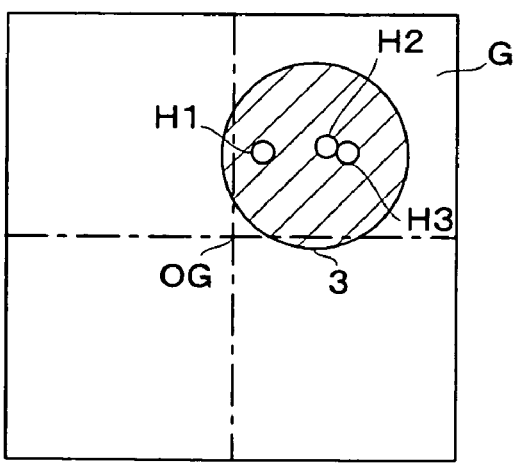
FIG. 8D is a plan view showing a transmission image of the subject when the focal point is rotated 225 degrees with respect to the start position.
Figure 9A:
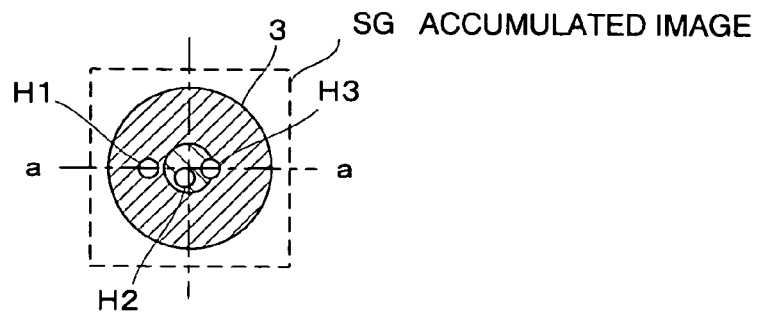
FIG. 9A is a plan view showing an accumulated image obtained by processing by the X-ray tomograph of the invention.
Figure 9B:
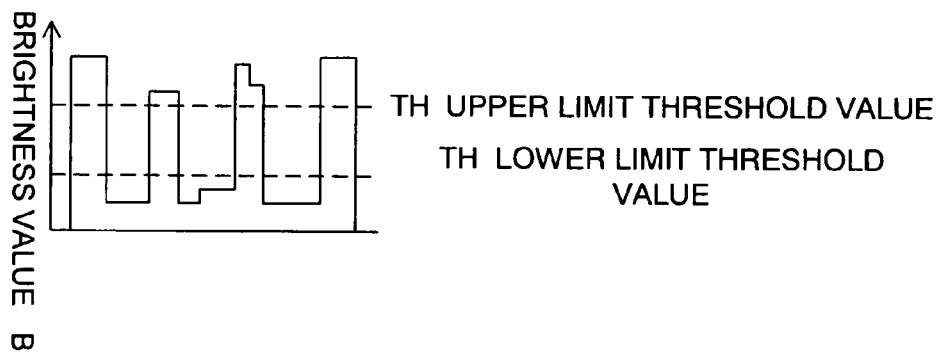
FIG. 9B is a view showing a luminance profile taken along line a-a of the accumulated image shown in FIG. 9A processed by the X-ray tomograph of the invention.
Figure 9C:
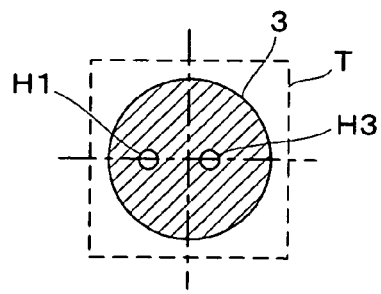
FIG. 9C is a plan view showing a tomographic image processed by the X-ray tomograph of the invention.

As shown in FIG. 6, the whole of the X-ray image of the subject 3 is moved such that its center is positioned on a circumference C with a radius R having the center 0G of the transmission images G as the center. At the same time, the hole H2 positioned outside of the tomographic plane S1 which passes through the center of the subject 3 as shown in FIG. 7 and FIG. 8A through FIG. 8D changes its positions within a circle with the center of the cutout images CG of the transmission images G0, G1, ..., Gi, ..., Gn determined as the center. As a result, the accumulated image SG has a small brightness value B of pixels at the position corresponding to the hole H2 because the brightness value B of the pixels at the position corresponding to the hole H2 cancel each other in the individual transmission images G0, G1, ..., Gi, ..., Gn as shown in FIG. 9A through FIG. 9C.

The computer 6 extracts pixels having the brightness value B between the upper limit threshold value TH and the lower limit threshold value TL from the individual pixels of the accumulated image SG1 to create the tomographic image T1 shown in FIG. 3. And, the tomographic image T1 is sent to and shown on the monitor 7.

Similarly, the computer 6 of the image processing device 2 creates square cutout images CGm0, CGm1, ..., CGmi, ..., CGmn with a center 0B, which is positioned on a virtual circle Cm having a radius Rm with respect to the transmission images G0, G1, ..., Gi, ..., Gn determined as the center, and accumulates the cutout images CGm0, CGm1, ..., CGmi, ..., CGmn to create the accumulated image SGm. And, pixels with the brightness value B between the upper limit threshold value TH and the lower limit threshold value TL are extracted from the pixels of the individual accumulated images SGm to create a tomographic image Tm corresponding to individual tomographic plane Sm.

Figure 10:
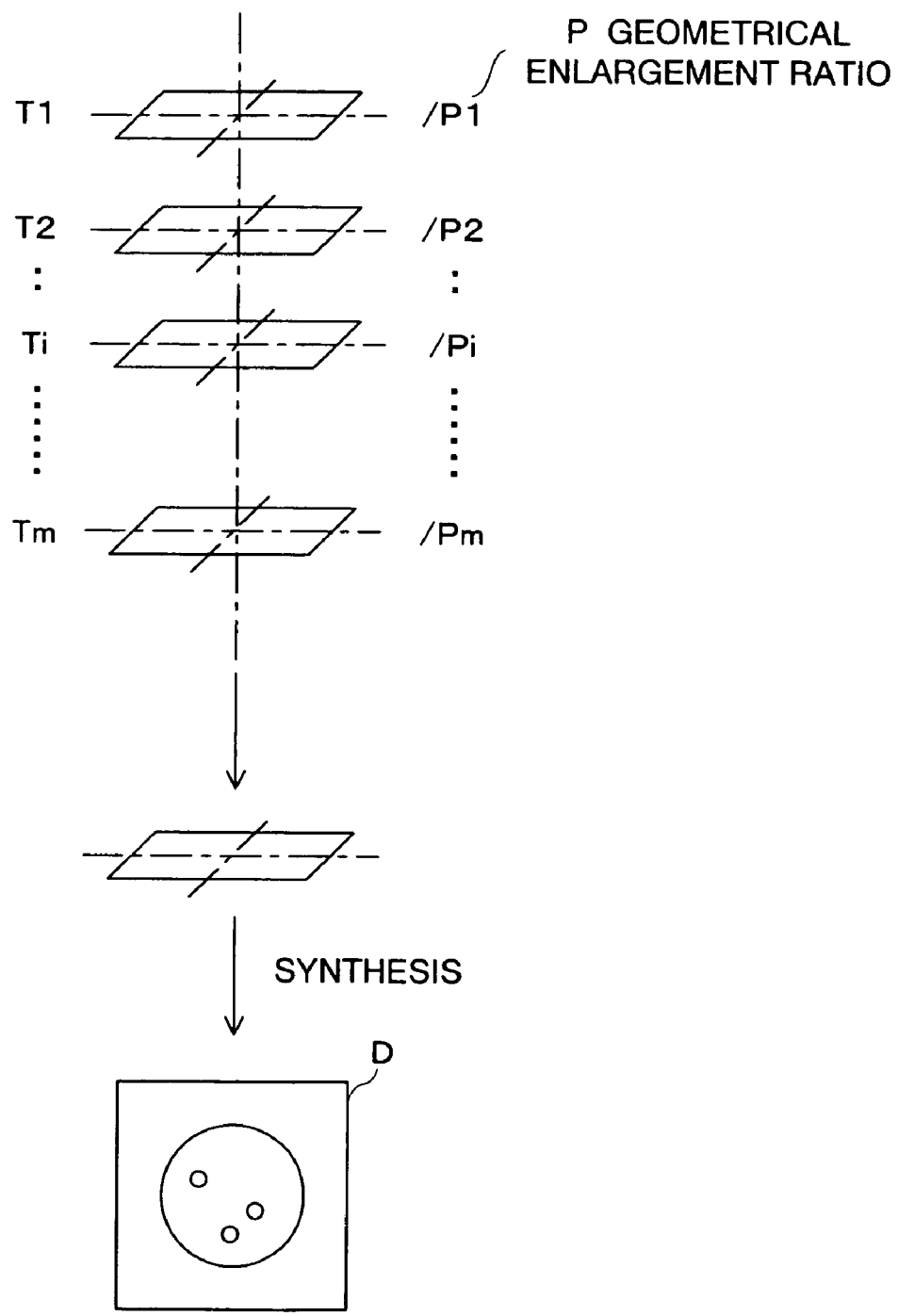
FIG. 10 is an explanatory view showing synthesis of tomographic images by the stereoradioscopic image constructing equipment of the invention.

Then, the computer 6 corrects geometrical enlargement ratios P1, P2, ..., Pi, ..., Pm of individual tomographic images T1, T2, ..., Ti, ..., Tm corresponding to individual tomographic planes S1, S2, ..., Si, ..., Sm as shown in FIG. 10. Specifically, the individual tomographic images T1, T2, ..., Ti, ..., Tm are divided by the geometrical enlargement ratios P1, P2, ..., Pi, ..., Pm, and the individual tomographic images T1, T2, ..., Ti, ..., Tm having corrected the geometrical enlargement ratios P1, P2, ..., Pi, ..., Pm are synthesized by the computer 6 to create a stereoradioscopic image D.

Thus, according to the above embodiment, an X-ray is radiated to the subject 3 while moving the position of the X-ray generating source 4b of the X-ray tube 4, and the transmission images G0, G1, ..., Gi, ..., Gn of the subject 3 by the X-rays with the different focal positions are received by the X-ray image receiving element 5. And, the received transmission images G0, G1, ..., Gi, ..., Gn are processed by the image processing section of the computer 6 to obtain the tomographic image T.

Specifically, it is configured that the X-ray generating source 4b of the X-ray tube 4 is moved along the circumference, the transmission images G0, G1, ..., Gi, ..., Gn of the subject 3 corresponding to the individual positions of the X-ray generating source 4b are accumulated to create the accumulated image SG, and the pixels with the brightness value B of the accumulated image SG between the prescribed upper limit threshold value TH and the prescribed lower limit threshold value TL are extracted to create the tomographic images T.

Therefore, the X-ray CT apparatus 1 which is a conventional X-ray transmission inspection apparatus is provided with a function to rotate the positions of the X-ray generating source 4b of the X-ray tube 4 along the circumference, so that the tomographic image T of the subject 3 can be obtained easily without disposing a movable mechanism for moving the X-ray tube 4 or the like. For example, a tomographic image of a soft subject 3 can also be obtained surely.

And, the stereoradioscopic image D can be obtained easily by synthesizing upon correcting the geometrical enlargement ratio P of the tomographic image T, so that the stereoradioscopic image constructing equipment can be made compact and inexpensive.

Besides, the tomographic images T corresponding to the individual tomographic planes S can be obtained by one rotation of the X-ray generating source 4b along the circumference, so that a photographing speed of the tomographic image T can be enhanced, and a time required to obtain the tomographic image T can be decreased regardless of the size of the subject 3 in comparison with the method to rotate and translate the X-ray tube or the subject. Therefore, if the subject 3 is a human, a burden on the subject can be reduced when photographing.

In the above-described embodiment, if the tomographic image T of the subject 3 can be obtained without fail, the X-ray generating source 4b can be moved along a variety of orbits other than the circumference, such as a figure of 8 in a planar view.

INDUSTRIAL APPLICABILITY

According to the present invention, an tomographic image of a subject can be obtained easily without provision of a movable mechanism for moving, for example, an X-ray generator, an X-ray image receiving element or a subject, and an tomographic image of a soft subject or the like can also be obtained securely.

What is claimed is:

1. An x-ray tomograph, comprising:
an X-ray generator configured to move a focal position and radiate x-rays toward a subject, the X-ray generator being fixed;
a planar X-ray image receiving element configured to receive a plurality of transmission images of the subject formed by the X-rays radiated from the X-ray generator while the focal position is moved, the planar X-ray image receiving element being fixed; and
an image processing section configured to create a tomographic image by processing the plurality of transmission images of the subject received by the X-ray image receiving element,
wherein the subject is fixed between the X-ray generator and the planar X-ray image receiving element, the X-ray generator has a radiation plane which is parallel to the planar X-ray image receiving element, the focal position of the X-ray generator is rotatable on a circumference on the radiation plane, and
wherein the image processing section cuts out images from the individual transmission images corresponding to individual focal positions of the X-ray generator and accumulates the cut-out images to create an accumulated image, each of the cut-out images has a virtual center which is positioned on a circumference with a radius R from a center of each of the transmission images.

2. The x-ray tomograph according to claim 1,
wherein the image processing section accumulates the transmission images of the subject corresponding to the individual focal positions of the x-ray generator to create the accumulated image and extracts pixels having a brightness value of the accumulated image between a prescribed upper limit threshold value and a lower limit threshold value to create the tomographic image.

3. The x-ray tomograph according to claim 2, wherein the image processing section creates the tomographic image of the subject for each of a plurality of tomographic planes which intersect in prescribed directions and are different from one another.

4. The x-ray tomograph according to claim 1, wherein the image processing section creates the tomographic image of the subject for each of a plurality of tomographic planes which intersect in prescribed directions and are different from one another.

5. A stereoradioscopic image constructing equipment, comprising:
an X-ray tomograph according to claim 1, further including a stereoradioscopic image constructing section configured to create a stereoradioscopic image by processing a plurality of tomographic images obtained by the X-ray tomograph.

6. The stereoradioscopic image constructing equipment according to claim 5,
wherein the stereoradioscopic image constructing section corrects geometrical enlargement ratios of the plurality of tomographic images obtained by the x-ray tomograph and combines the corrected tomographic images to create a stereoradioscopic image.

* * * * *